(12) United States Patent  
Katsu et al.

(10) Patent No.: US 6,734,306 B2  
(45) Date of Patent: May 11, 2004

(54) N-BENZENESULFONYL L-PROLINE COMPOUNDS AS BRADYKININ ANTAGONISTS

(75) Inventors: Yasuhiro Katsu, Tokyo (JP); Makoto Kawai, Tokyo (JP); Hiroki Koike, Tokyo (JP); Seiji Nukui, Tokyo (JP)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/010,863

(22) Filed: Dec. 5, 2001

(65) Prior Publication Data

US 2002/0128271 A1 Sep. 12, 2002

Related U.S. Application Data

(60) Provisional application No. 60/251,225, filed on Dec. 5, 2000.

(51) Int. Cl.$^7$ ............................................. C07D 401/14

(52) U.S. Cl. ........................................ 544/363; 546/177

(58) Field of Search .......................................... 544/363

(56) References Cited

U.S. PATENT DOCUMENTS 6,211,181 B1 * 4/2001 Dodey et al. .......... 514/253.06

* cited by examiner

*Primary Examiner*—Patricia L. Morris  
(74) *Attorney, Agent, or Firm*—Charles W. Ashbrook; David R. Kurlandsky

(57) ABSTRACT

This invention provides a compound of the formula (I):

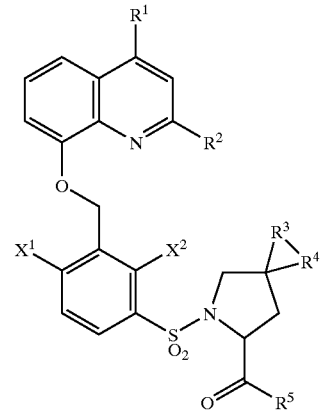

or the pharmaceutically acceptable salts thereof wherein $X^1$ and $X^2$ are halo; $R^1$ and $R^2$ are independently hydrogen or $C_{1-4}$ alkyl; $R^3$ and $R^4$ are each hydrogen or halo; and $R^5$ is (a) —$C_{3-9}$ diazacycloalkyl optionally substituted with $C_{5-11}$ azabicycloalkyl;

(b) —$C_{3-9}$ azacycloalkyl-NH—($C_{5-11}$ azabicycloalkyl optionally substituted with $C_{1-4}$ alkyl);

(c) —NH—$C_{1-3}$ alkyl-C(O)—$C_{5-11}$ diazabicycloalkyl;

(d) —NH—$C_{1-3}$ alkyl-C(O)—NH—$C_{5-11}$ azabicycloalkyl, the $C_{5-11}$ azabicycloalkyl being optionally substituted with $C_{1-4}$ alkyl;

(e) —$C_{3-9}$ azacycloalkyl optionally substituted with $C_{3-9}$ azacycloalkyl; or (f) —NH—$C_{1-5}$ alkyl-NH—C(O)—$C_{4-9}$ cycloalkyl-$NH_2$.

These compounds are useful for the treatment of medical conditions mediated by bradykinin such as inflammation, allergic rhinitis, pain, etc. This invention also provides a pharmaceutical composition comprising the above compound.

5 Claims, No Drawings

N-BENZENESULFONYL L-PROLINE COMPOUNDS AS BRADYKININ ANTAGONISTS

This application claims priority under 35 U.S.C. §119(e) of U.S. application serial No. 60/251,225 filed Dec. 5, 2000, which application is hereby incorporated by reference herein.

TECHNICAL FIELD

This invention relates to novel N-benzenesulfonyl L-proline compounds. These compounds are useful as antagonists of bradykinin, and are thus useful in the treatment of inflammation, asthma, allergic rhinitis, pain or the like in mammalian, especially humans. The present invention also relates to a pharmaceutical composition comprising the above compounds.

BACKGROUND ART

Bradykinin ("BK") is generated under normal conditions in mammalia by the action of various plasma enzymes such as kallikrein on high molecular weight kininogens. It is widely distributed in mammals, and relates its two receptor subtypes, $B_1$ and $B_2$. The actions of BK at the $B_2$ receptor include mainly contraction of arterial and venous preparations, although it can cause relaxation of peripheral resistance vessels as well.

Many of the more important functions of BK, such as increases in vascular permeability, pain, and vasodilatation, however, are mediated by the $B_2$ receptor. These effects at the $B_2$ receptor are believed to be responsible for BK's role in numerous diseases, such as inflammation, cardiovascular disease, pain, and the common cold. Hence antagonists at the $B_2$ receptor should find considerable therapeutic applications. Most of the efforts in this area thus far have been directed at peptidic analogues of the BK structure, some of which have been studied as analgesics and antiinflammatory agents.

Numerous N-benzenesulfonyl L-proline compounds as a $B_2$ antagonist have been synthesized, and disclosed in a number of patent publications such as international publication Nos. WO 97/41104, WO 96/13485, WO 99/00387, WO 98/24783, WO 98/03503, WO 97/24349, WO 97/07115 and WO 96/40639.

International Publication Number WO 98/24783, WO 98/03503, WO 97/24349, WO 97/07115 disclose a variety of N-benzenesulfonyl L-proline compounds as antagonists of bradykinin.

It would be desirable if there were provided a non-peptide antagonist of the $B_2$ receptor, having an improved $B_2$ antagonistic activity and a good metabolic stability against human liver microsomes.

BRIEF DISCLOSURE OF THE INVENTION

The present invention provides a compound of the following formula:

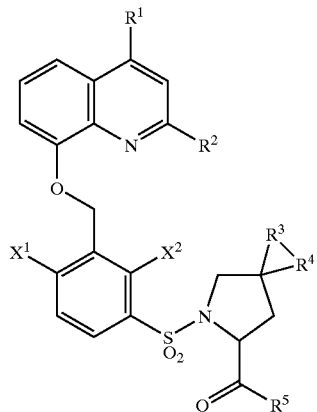

(I)

or the pharmaceutically acceptable salts thereof wherein
$X^1$ and $X^2$ are independently halo or $C_{1-4}$ alkyl;
$R^1$ and $R^2$ are independently hydrogen or $C_{1-4}$ alkyl;
$R^3$ and $R^4$ are independently hydrogen or halo; and
$R^5$ is
(a) —$C_{3-9}$ diazacycloalkyl optionally substituted with $C_{5-11}$ azabicycloalkyl;
(b) —$C_{3-9}$ azacycloalkyl-NH—($C_{5-11}$, azabicycloalkyl optionally substituted with $C_{1-4}$ alkyl);
(c) —NH—$C_{1-3}$ alkyl-C(O)—$C_{5-11}$ diazabicycloalkyl;
(d) —NH—$C_{1-3}$ alkyl-C(O)—NH—$C_{5-11}$ azabicycloalkyl, the $C_{5-11}$ azabicycloalkyl being optionally substituted with $C_{1-4}$ alkyl;
(e) —$C_{3-9}$ azacycloalkyl optionally substituted with $C_{3-9}$ azacycloalkyl; or
(f) —NH—$C_{1-5}$ alkyl-NH—C(O)—$C_{4-9}$ cycloalkyl-$NH_2$.

The N-benzenesulfonyl L-proline compounds of this invention have an antagonistic action towards bradykinin and are thus useful in therapeutics, particularly for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, pancreatitis, neovascularization, corneal haze, glaucoma, ocular pain, ocular hypertension or the like in mammalian, especially humans.

The N-benzenesulfonyl L-proline compounds of this invention have an antagonistic action towards bradykinin and are thus useful in therapeutics, particularly for the treatment of Amyotrophic lateral sclerosis, Huntington's disease, Parkinson's disease, multiple sclerosis, stroke, head trauma, post-surgical brain edema, brain edema (general), cytotoxic brain edema (such as that associated with brain tumors, stroke, head trauma, etc.), brain edema associated with metabolic diseases (renal failure, pediatric metabolic diseases, etc.), rheumatoid arthritis, osteoarthritis, migraine, neuropathic pain, pruritis, brain tumor, pseudotumor cerebri, glaucoma, hydrocephalus, spinal cord trauma, spinal cord edema, neurodegenerative diseases, respiratory diseases, diuresis, natriuresis calciuresis, COPD (chronic obstructive pulmonary disease), post-traumatic brain injury, itching, sepsis or the like in mammalian, especially humans.

The present invention provides a pharmaceutical composition for the treatment of disease conditions mediated by bradykinin, in a mammalian subject, which comprises administering to said subject a therapeutically effective amount of a compound of formula (I).

Further, the present invention also provides a pharmaceutical composition for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, pancreatitis, neovascularization, corneal haze, glaucoma, ocular pain, ocular hypertension or the like, which comprises a therapeutically effective amount of the N-benzenesulfonyl L-proline compound of formula (I) or its pharmaceutically acceptable salt together with a pharmaceutically acceptable carrier.

Further, the present invention also provides a pharmaceutical composition for the treatment of Amyotrophic lateral sclerosis, Huntington's disease, Parkinson's disease, Multiple sclerosis, Stroke, head trauma, Post-surgical brain edema, Brain edema (general), Cytotoxic brain edema (such as that associated with brain tumors, stroke, head trauma, etc.), Brain edema associated with metabolic diseases (renal failure, pediatric metabolic diseases, etc.), Rheumatoid arthritis, Osteoarthritis, Migraine, Neuropathic Pain, Pruritis, Brain Tumor, Pseudotumor cerebri, Glaucoma, Hydrocephalus, Spinal cord trauma, Spinal cord edema, neurodegenerative diseases, respiratory diseases, diuresis, natriuresis calciuresis, COPD (chronic obstructive pulmonary disease), post-traumatic brain injury, itching or Sepsis, which comprises a therapeutically effective amount of a compound of formual (I) or its pharmaceutically acceptable carrier.

Also, the present invention provides a method for the treatment of disease conditions mediated by bradykinin, in a mammalian subject, which comprises administering to said subject a therapeutically effective amount of a compound of formula (I).

Further, the present invention provides a method for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, pancreatitis, neovascularization, corneal haze, glaucoma, ocular pain, ocular hypertension or the like, in a mammalian subject, which comprises administering to said subject a therapeutically effective amount of a compound of formula (I).

DETAILED DESCRIPTION OF THE INVENTION

As used herein, the term "halo" is fluoro, chloro, bromo or iodo (preferably fluoro or chloro).

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "$C_{4-9}$ cycloalkyl" means monocyclic alkyl having 4 to 9 carbon atoms, such as cyclobutyl, cyclopentyl, cycloheptyl, cyclohexyl, and the like.

As used herein, the term "$C_{3-9}$ azacycloalkyl, $C_{3-9}$ diazacycloalkyl, $C_{5-11}$ azabicycloalkyl or $C_{5-11}$ diazabicycloalkyl" means a group wherein one or two carbons of mono- or bicyclic alkyl ring components are substituted by nitrogen atoms, included, but not limited to, azetidinyl, piperazinyl, piperidino, piperidinyl, pyrrolidinyl, azabicyclo[3.3.0]octyl, quinuclidinyl, azabicyclo[3.2.1]octyl, azabicyclo[3.3.1]nonyl, azabicyclo[2.2.2]octyl or diazabicyclo[3.2.1]octyl.

In the formula (I), $R^5$ is preferably (a) —$C_{3-9}$ diazacycloalkyl optionally substituted with $C_{5-11}$ azabicycloalkyl or (c) —NH—$C_{1-3}$ alkyl-C(O)—$C_{5-11}$ diazabicycloalkyl, more preferably (a) —$C_{4-8}$ diazacycloalkyl optionally substituted with $C_{6-10}$ azabicycloalkyl or —NH—$C_{1-3}$ alkyl-C(O)—$C_{6-10}$ diazabicycloalkyl, further preferably azabicyclo[2.2.2]octyl-piperazinyl, diazabicyclo[3.2.1]octyl-oxomethylamino or diazabicyclo[3.2.1]octyl-oxoethylamino, and most preferably azabicyclo[2.2.2]octyl-piperazinyl or diazabicyclo[3.2.1]octyl-oxomethylamino.

Preferred compounds of this invention are those of the formula (I) wherein $X^1$ and $X^2$ are chloro;

$R^1$ and $R^2$ are independently hydrogen, methyl or ethyl;

$R^3$ and $R^4$ are independently hydrogen or fluoro; and $R^5$ is
  (a) —$C_{4-8}$ diazacycloalkyl optionally substituted with $C_{6-10}$ azabicycloalkyl;
  (b) —$C_{3-6}$ azacycloalkyl-NH—($C_{6-10}$ azabicycloalkyl optionally substituted with $C_{1-4}$ alkyl);
  (c) —NH—$C_{1-3}$ alkyl-C(O)—$C_{6-10}$ diazabicycloalkyl;
  (d) —NH—$C_{1-3}$ alkyl-C(O)—NH—$C_{6-10}$ azabicycloalkyl, the $C_{6-10}$ azabicycloalkyl being optionally substituted with $C_{1-4}$ alkyl;
  (e) —$C_{4-8}$ azacycloalkyl optionally substituted with $C_{4-8}$ azacycloalkyl; or
  (f) —NH—$C_{1-5}$ alkyl-NH—C(O)—$C_{58}$ cycloalkyl-NH$_2$.

Much preferred compounds of this invention are those of the formula (I) wherein $R^1$ and $R^2$ are methyl; $R^3$ and $R^4$ are hydrogen; and $R^5$ is azabicyclo[2.2.2]octyl-piperazinyl, azabicylo[3.2.1]octanylaminoazetidinyl, diazabicyclo[3.2.1]octyl-oxomethylamino, diazabicyclo[3.2.1]octyl-oxoethylamino, methylazabicyclo[3.2.1]octyl-aminooxomethylamino, methylazabicyclo[3.2.1]octyl-aminooxoethylamino, ethylazabicyclo[3.2.1]octyl-aminooxomethylamino, piperidinopiperidinyl, [[(aminocyclohexyl)carbonyl]amino]propylamino or [[(aminocyclohexyl)carbonyl]amino]butylamino.

Also, preferred compounds of this invention are those of the formula (I) wherein $R^5$ is azabicyclo[2.2.2]octyl-piperazinyl, azabicylo[3.2.1]octanylaminoazetidinyl, diazabicyclo[3.2.1]octyl-oxomethylamino, methylazabicyclo[3.2.1]octyl-aminooxomethylamino, piperidinopiperidinyl or [[(aminocyclohexyl)carbonyl]amino]propylamino.

Preferred individual compounds of this invention are:

8-[[3-[[(2S)-2-[[4-[(3S)-1-Azabicyclo[2.2.2]oct-3-yl]-1-piperazinyl]carbonyl]pyrrolidinyl]sulfonyl]-2,6-dichlorobenzyl]oxy]-2,4-dimethylquinoline; and (2S)-N-[2-(3,8-Diazabicyclo[3.2.1]oct-3-yl)-2-oxoethyl]-1-[[2,4-dichloro-3-[[(2,4-dimethyl-8-quinolinyl)oxy]methyl]phenyl]sulfonyl]-2-pyrrolidinecarboxamide, and a salt thereof.

General Synthesis

The N-benzenesulfonyl L-proline compounds of formula (I) of this invention may be prepared by a variety of synthetic methods.

Preparation Method A:

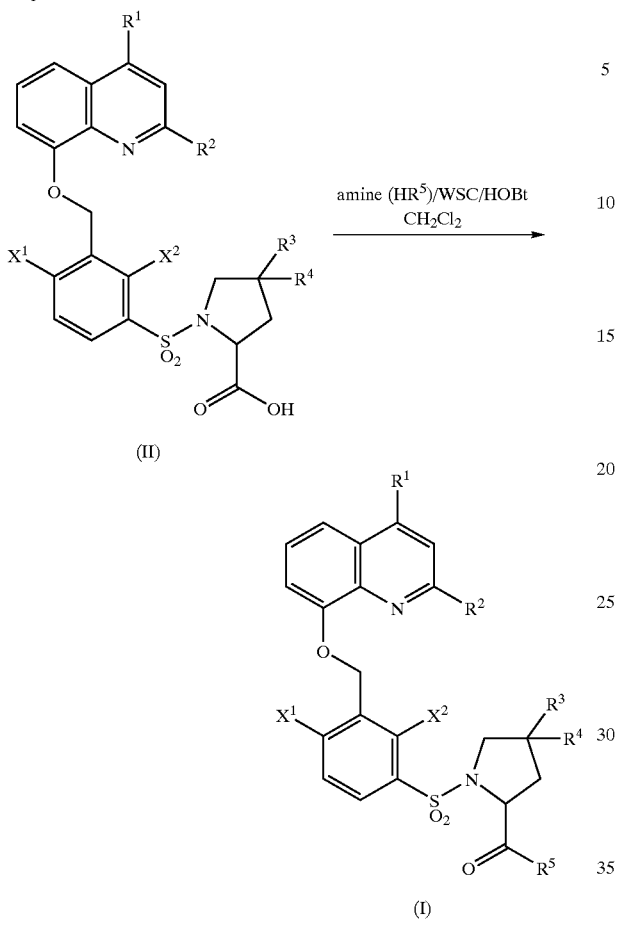

(wherein $X^1$, $X^2$, $R^1$, $R^2$, $R^3$, $R^4$ and $R^5$ are as already defined; and WSC is 1-[3-(dimethylamino)propyl]-3-ethylcarbodiimide hydrochloride, HOBt is 1-hydroxybenzotriazole hydrate.

Scheme A-1

To a stirred solution of the acid of formula (II) (150 mg, 0.294 mmol) and amine H-$R^5$ (0.441 mmol) in $CH_2Cl_2$ (15 mL) were added HOBt (67 mg, 0.441 mmol) and WSC (84 mg, 0.441 mmol) at room temperature and the mixture was stirred overnight. To the mixture was added $H_2O$ (5 mL) and the organic layer was separated, washed with saturated aqueous $NaHCO_3$, brine, dried over $MgSO_4$, filtered and concentrated in vacuo. Column chromatography (NH gel, 200–350 mesh, 8 g, $CH_2Cl_2$/MeOH=99/1 to 90/10) afforded the coupling product including a compound of formula (I).

In the described method A, 1,3-diisopropylcarbodiimide in place of WSC, t-BuOH—$CH_2Cl_2$(1-1), DMF, or AcOEt in place of $CH_2Cl_2$ were also used. For purification process, appropriate regins or solid-phase extraction method was also utilized when the small amount of the starting material (II) (about 50 Smol) were used.

To a stirred solution of the coupling product including a compound of formula (I) (0.0964 mmol) in MeOH was added HCl-MeOH (2.9 mL) and the mixture was stirred for 15 minutes. Then the solvent was removed in vacuo to provide the HCl salt.

Alternately, the N-benzenesulfonyl L-proline compounds of formula (Ia-II) were prepared by reaction of a compound (III) with a compound of formula (IV) as indicated in the following Scheme A-II.

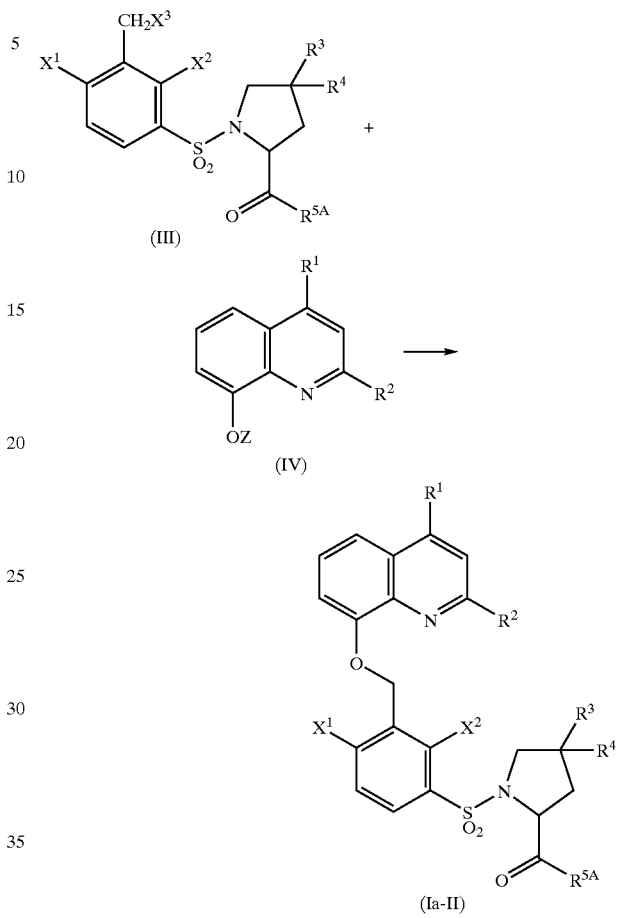

(wherein R is hydroxy, $C_{1-4}$ alkoxy (such as methoxy and ethoxy) or $R^5$; $X^3$ is halo; and the other symbols are as already defined are as already defined)

Scheme A-II

This method utilizes a synthesis as described in WO97/07115. This reaction is carried out in a suitable reaction-inert solvent (anhydrous). Suitable solvents include, for example, aromatic hydrocarbons such as benzene, toluene and xylene; alcohols such as methanol, ethanol, propanol and butanol; ethers such as diethyl ether, dioxane and tetrahydrofuran; halogenated hydrocarbons such as methylene dichloride, chloroform, dichloromethane and dichloroethane; amides such as N,N-dimethylformamide; and nitrites such as acetonitrile. This reaction is carried out at a temperature between −10° C. and 100° C., preferably from 0° C. to 50° C. for 5 minutes to 24 hours, preferably 30 minutes to 5 hours.

In addition, the compounds (III) and (IV) which can be used herein may be either already known or may be prepared according to the reported methods.

Preparation Method B

The compounds of formula (III) was prepared by the reaction of a compound (V) with a compound of formula (VI) as indicated in the following Scheme B.

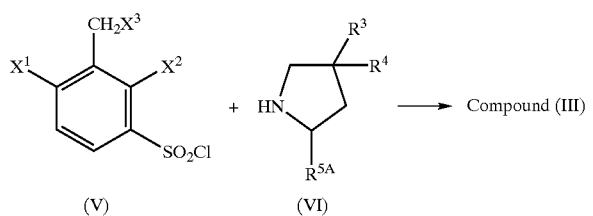

(wherein X³ is halo; and the other symbols are as already defined)

Scheme B

This method utilizes a synthesis as described in WO97/07115. This reaction is carried out in the presence of base in a suitable reaction-inert solvent. Suitable base includes, for example, triethylamine. Suitable solvents include, for example, aromatic hydrocarbons such as benzene, toluene and xylene; alcohols such as methanol, ethanol, propanol and butanol; ethers such as diethyl ether, dioxane and tetrahydrofuran; halogenated hydrocarbons such as chloroform, dichloromethane and dichloroethane; amides such as N,N-dimethylformamide; and nitrites such as acetonitrile. This reaction is carried out at a temperature between −10° C. and 100° C., preferably from 0° C. to 40° C. for 5 minutes to 24 hours, preferably 30 minutes to 3 hours.

The compounds of formula (I), and the intermediates above-mentioned preparation methods can be isolated and purified by conventional procedures such as recrystallization or chromatographic purification.

The optically active compounds of this invention can be prepared by several methods known to a skilled person in the art. For example, the optically active compounds of this invention may be obtained by chromatographic separation or fractional crystallization from the final compounds or the intermediates in racemic form thereof. Alternatively, the optically active compounds may be prepared by optically selective reaction, enzymatic hydrolysis or reactions using optically active intermediates.

The N-benzenesulfonyl L-proline compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The present invention includes salt forms of the compounds (I) as obtained above.

Insofar as the N-benzenesulfonyl L-proline compounds of this invention are basic compounds, they are capable of forming a wide variety of different salts with various inorganic and organic acids.

The acids which are used to prepare the pharmaceutically acceptable acid addition salts of the aforementioned N-benzenesulfonyl L-proline base compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate). The acid addition salts can be prepared by conventional procedures.

The N-benzenesulfonyl L-proline compounds of the present invention of formula (I) exhibit significant bradykinin receptor-binding activity and therefore, are of value in the treatment of a wide variety of clinical conditions in mammals, especially human. Such conditions include inflammation, cardiovascular disease, pain, common cold, allergies, asthma, pancreatitis, burns, virus infection, head injury, multiple trauma and the like.

Therefore, these compounds are readily adapted to therapeutic use as bradykinin antagonists for the control and/or treatment of any of the aforesaid clinical conditions in mammals, including humans.

Also, the compounds of formula (I) may be expected more effective therapeutic effects with being co-administered with $H_1$-antagonist.

Further, the present invention also encompasses a pharmaceutical composition for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, cystitis, pancreatitis, amyotrophic lateral sclerosis, Huntington's disease, Parkinson's disease, multiple sclerosis, stroke, head trauma, post-surgical brain edema, brain edema (general), cytotoxic brain edema (such as that associated with brain tumors, stroke, head trauma, etc.), brain edema associated with metabolic diseases (renal failure, pediatric metabolic diseases, etc.), rheumatoid arthritis, osteoarthritis, migraine, neuropathic pain, pruritis, brain tumor, pseudotumor cerebri, glaucoma, hydrocephalus, spinal cord trauma, spinal cord edema, neurodegenerative diseases, respiratory diseases, diuresis, natriuresis calciuresis, COPD (chronic obstructive pulmonary disease), post-traumatic brain injury, itching, sepsis, or the like, which comprises a therapeutically effective amount of the N-benzenesulfonyl L-proline compound of formula (I) and H1-antagonist or their pharmaceutically acceptable salt together with a pharmaceutically acceptable carrier.

The compounds of the invention may advantageously be employed in combination with one or more other therapeutic ingredients selected from an antibiotic, anti-fungal, or anti-viral agent, an anti-histamine, a non-steroidal anti-inflammatory drug or disease modifying anti-rheumatic drug.

The combination with an anti-histamine ($H_1$ antagonist) is particularly favoured for use in the prophylaxis and treatment of asthma and rhinitis. Examples of anti-histamine are chlorpheniramine, brompheniramine, clemastine, ketotifen, azatadine, loratadine, terfenadine, cetirizine, astemizole, tazifylline, levocabastine, diphenhydramine, temelastine, etolotifen, acrivastine, azelastine, ebastine, mequitazine, KA-398, FK-613, mizolastine, MDL-103896, levocetirizine, mometasone furoate, DF-1111301, KC-11404, carebastine, ramatroban, desloratadine, noberastine, selenotifen, alinastine, E-4716, efletirizine, tritoqualine, norastemizole, ZCR-2060, WY-49051, KAA-276, VUF-K-9015, tagorizine, KC-11425, epinastine, MDL-28163 terfenadine, HSR-609, acrivastine and BMY-25368.

Method for Assessing Biological Activities

The activity of the N-benzenesulfonyl L-proline compounds of the present invention, as bradykinin antagonists, is determined by their ability to inhibit the binding of bradykinin at its receptor sites in recombinant human bradykinin $B_2$ receptor expressing CHO-KI cells (from Receptor Biology, Inc.) employing radioactive ligands.

The bradykinin antagonist activity of the N-benzenesulfonyl L-proline compounds is evaluated by using the standard assay procedure described in, for example, Baenziger N. L., Jong Y-J. I., Yocum S. A., Dalemar L. R., Wilhelm B., Vaurek R., Stewart J. M., Eur. J. Cell Biol., 1992, 58, 71–80. This method essentially involves determining the concentration of the individual compound required to reduce the amount of radiolabelled bradykinin ligands by 50% at their receptor sites in CHO-K1 cells, thereby affording characteristic $IC_{50}$ values for each compound tested.

More specifically, the assay is carried out as follows. First, rat, guinea pig or monkey ileum tissues are minced and suspended in 25 mM piperazine-N,N'-bis (2-ethanesulfonic acid (PIPES) buffer (pH 6.8) containing 0.1 mg/ml of soybean trypsin inhibitor. Then, the tissues are homogenized using a Polytron homogenizer at setting 7 for 30 seconds three times, and then rehomogenized with a Teflon-coated homogenizer. The homogenized suspension was centrifuged at 1,200× g for 15 minutes. The pellet was rehomogenized and then centrifuged at 1,200× g for 15 minutes. These supernatant were centrifuged at 10,000× g for 60 minutes. The tissue pellets, CHO-K1 cell membrane are suspended in 25 mM PIPES buffer (pH6.8) containing 1.25 mM dithiothreitol, 1.75 µg/ml bacitracin, 1 mM o-phenanthroline, 18.75 µM captopril, 1.25 mg/ml bovine serum albumin (BSA), to prepare tissue/cell suspensions. Then, 10 µl of test compound solution dissolved in phosphate buffered saline (PBS, pH 7.5) containing 2% DMSO (final) and 0.1% BSA(w/v) or 10 ml of 12.5 mM bradykinin in PBS (pH 7.5) containing 0.1% BSA (w/v) are placed in a reaction 96-well plate. 15 µl of 8.3 nM [3H]bradykinin is added to the compound solution or bradykinin solution in the 96-well plate. Finally 100 µl of the tissue or cell suspension are added to the mixture in the plate, and incubated at room temperature for 1 hour under the dark. After incubation, the resultant product in the reaction plates is filtered through 0.1% polyethylenimine presoaked LKB filermat. The filtrate is washed using a Skatron auto cell harvester. The tissue bound radioactivity is determined using a LKB betaplate counter. The $IC_{50}$ value is determined using the equation:

$$Bound=B_{max}/(1+[I]/IC_{50})$$

wherein [I] means the concentration of the test compound.

All compounds prepared in the working examples as described below were tested by this method, and showed an $IC_{50}$ value of 0.1 nM to 4 nM in CHO-KL cells with respect to inhibition of binding at its receptor.

The most preferred compounds prepared in the working examples as described below were tested by this method, and showed an $IC_{50}$ value of 0.5 nM to 3.3 nM in CHO-K1 cells with respect to inhibition of binding at its receptor.

The possibility of drug—drug interaction of the N-benzenesulfonyl L-proline compounds of the present invention, as bradykinin antagonists, is determined by their ability to inhibit the testosterone 6□-hydroxylase activity raised by CYP3A4 which is most abundant subtype of cytochrome P-450 in human.

CYP3A4 interaction assay

This method essentially involves determining the concentration of the individual compound required to reduce the amount of 67-hydroxytestosterone by 50%.

More specifically, the assay is carried out as follows. Human liver microsomes (0.2 mg/ml) were mixed with appropriate concentrations of kinin B2 antagonist. Then, incubated with the presence of 50 µM testosterone, 1.3 mM $NADP^+$, 0.9 mM NADH, 3.3 mM glucose-6-phosphate, 3.3 mM $MgCl_2$, and glucose-6-phosphate dehydrogenase (8 units/ml) in a total volume of 0.2 ml of 100 mM potassium phosphate buffer, pH 7.4, at 37° C. After incubation (20 minutes), 10 µl of methylalchol containing internal standard was withdrawn. The medium was filtrated by membrane filter with centrifugation at 1,800× g for 10 minutes, and the resulting filtrate was taken.

□□6□-hydroxylated metabolite of testosterone in samples was analyzed by HPLC. A sample of 20 µl was injected to the HPLC system equipped with a Polymer Cl 8 column (2.0×75 mm). The mobile phase consisted of 24% to 66% acetonitorile linear gradient including 10 mM ammonium phosphate, and with a flow rate of 0.35 ml/min.

The $IC_{50}$ value is determined using the equation:

$$Activity=Activity_{contol}/(1+[I]/IC_{50})$$

wherein [I] means the concentration of the test compound.

The most preferred compounds as memtined above of Working Examples showed $IC_{50}$ values of more than 10 µM.

Human Liver Microsome Assay $T_{12}$ value against human liver microsome was calculated by conventional procedure. More specifically, human liver microsomes (0.2 mg/ml) were mixed with 1 µM of kinin B2 antagonist and incubated with in the presence of 1.3 mM $NADP^+$, 0.9 mM NADH, 3.3 mM glucose-6-phosphate, 3.3 mM $MgCl_2$, and glucose-6-phosphate dehydrogenase (8 units/ml) in a total volume of 1.2 ml of 100 mM potassium phosphate buffer, pH 7.4, at 37° C. At specified incubation times (0, 5, 10, 30 minutes), an aliquot of 100 µl was withdrawn from the reaction mixture and mixed with 1 ml of acetonitrile containing internal standard. Protein was precipitated by centrifugation at 1,800× g for 10 minutes, and the resulting supernatant was taken.

Bradikinin B2 antagonist in samples were analyzed by LS/MS/MS, in a Sciex API-300 mass spectrometer linked with a Hawlett-Pakkered HP1100 HPLC system. A sample of 20 µl was injected to the HPLC system equipped with a Wakosil II 5C18 HG column (2.0×150 mm). The mobile phase consisted of 80% acetonitorile including 10 mM ammonium acetate, and the elution was isocratic with a flow rate of 0.3 ml/min. Part of the eluent from the HPLC column was introduced into the atmospheric ionization source via an ion spray interface. $T_{1/2}$ value is determined using the equation:

$$T_{1/2}=0.693/k$$

wherein k is elimination rate constant of the test compound.

The compounds of the formula (I) exhibit excellent biological activity in vitro and in vivo as bradykinin antagonists. Additionally, the compound of the formula (I) was stable against metabolism in human liver microsomes assay experiments. The most preferred compounds of Working Examples showed $T_{112}$ values of more than 10 minutes.

The compound of this invention showed a good $IC_{50}$ in CHO-K1 cells and a good $T_{1/2}$ value, which are essential for a practical drug.

The N-benzenesulfonyl L-proline compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254}$s precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM) or Fuji Silysia Chromatorex DU3050 (Amino Type, 30–50 $\mu$m). Low-resolution mass spectral data (EI) were obtained on a Automass 120 (JEOL) mass spectrometer. Low-resolution mass spectral data (ESI) were obtained on a Quattro II (Micromass) or ZMD (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.).

Chemical symbols have their usual meanings; b.p. (boiling point), m.p. (melting point), l (liter(s)), ml (milliliter(s)), g (gram(s)), mg(milligram(s)), mol (moles), mmol (millimoles), eq. (equivalent(s)).

Example 1

8-[[3-[[(2S)-2-[[4-[(3S)-1-AZABICYCLO[2.2.2]OCT-3-YL]-1-PIPERAZINYL]CARBONYL]PYRROLIDINYL]SULFONYL]-2,6-DICHLOROBENZYL]OXY]-2,4-DIMETHYLQUINOLINE, HCL SALT

A. 1-[(3S)-1-Azabicyclo[2.2.2]oct-3-yl]-4-benzyl-2,6-piperazinedione

To a solution of N-benzyliminodiacetic acid (2.23 g, 10.0 mmol) in THF (30 mL) was added 1,1'-carbonylbis-1H-imidazole (3.57 g, 22.0 mmol) at room temperature under nitrogen atmosphere. The resulting mixture was stirred at reflux temperature for 30 min (until the evolution of $CO_2$ gas ceased, giving a clear solution), then cooled to room temperature. To the resulting mixture was added a solution of (3S)-3-aminoquinuclidine dihydrochloride (2.00 g, 10.0 mmol) and triethylamine (3.06 mL, 22.0 mmol) in THF (10 mL) stirred at room temperature under nitrogen atmosphere for 30 min via a cannula. The combined reaction mixture was stirred under reflux for 24 h, then cooled to room temperature and quenched with $H_2O$ (10 mL). The organic layer was extracted with EtOAc (50×2 mL) and the combined organic layers were dried over $MgSO_4$, concentrated in vacuo. The residue was purified by column chromatography (NH gel, 200–350 mesh, 150 g, EtOAc) to give a product (2.17 g, 69%) as a white solid.

$^1$H NMR (CDCl$_3$) δ: 7.39–7.27 (m, 5 H), 4.73–4.66 (m, 1 H), 3.77–3.69 (m, 1 H), 3.60 (s, 2 H), 3.38 (s, 4 H), 3.34–3.29 (m, 1 H), 3.02–2.93 (m, 1 H), 2.90–2.75 (m, 3 H), 1.91–1.61 (m, 4 H), 1.38–1.28 (m, 1 H)

B. (3S)-3-(4-Benzyl-1-piperazinyl)-1-azabicyclo[2.2.2]octane

To a solution of 1-[(3S)-1-azabicyclo[2.2.2]oct-3-yl]-4-benzyl-2,6-piperazinedione (1.90 g, 6.00 mmol) in 1,4-dioxane (40 mL) was added LiAlH$_4$ (911 mg, 24.0 mmol) at room temperature under nitrogen atmosphere. The resulting suspension was stirred under reflux for 3.5 h, then cooled to 0° C. The mixture was diluted with Et$_2$O (80 mL), then treated carefully with Na$_2$SO$_4$10 H$_2$O (9.1 g) and anhydrous KF (1 g). After the resulting white suspension was stirred vigorously at room temperature for 30 min, the white precipitate was removed by filtration through a pad of celite. The filtrate was concentrated in vacuo and the residue was purified by column chromatography (NH gel, 200–350 mesh, 40 g, EtOAc) to give a product (1.39 g, 81%) as a white solid.

$^1$H NMR (CDCl$_3$) 67 : 7.32–7.24 (m, 5 H), 3.51 (s, 2 H), 3.01–1.98 (m, 16 H), 1.83–1.59 (m, 2 H), 1.48–1.40 (m, 1 H), 1.30–1.21 (m, 1 H)

C. (3S)-3-(1-Piperazinyl)-1-azabicyclo[2.2.2]octane

A mixture of (3S)-3-(4-benzyl-1-piperazinyl)-1-azabicyclo[2.2.2]octane (1.25 g, 4.37 mmol) and 400 mg of Pd(OH)$_2$ (20 wt % on carbon) in MeOH (60 mL) was stirred at room temperature under hydrogen atmosphere (4 atm) for 6 h. The reaction mixture was filtered through a pad of celite and the filtrate was concentrated in vacuo to give a product (850 mg, quant.).

$^1$H NMR (CDCl$_3$) δ: 3.01–2.00 (m, 16 H), 1.81–1.65 (m, 2 H), 1.50–1.36 (m, 1 H), 1.36–1.20 (m, 1 H)

D. 8-[[3-[[(2S)-2-[[4-[(3S)-1-Azabicyclo[2.2.2]oct-3-yl]-1-piperazinyl]carbonyl]pyrrolidinyl]sulfonyl]-2,6-dichlorobenzyl]oxy]-2,4-dimethylquinoline. HCl salt This compound was prepared by a procedure similar to that described in method A and AcOEt was used for the extraction solvent. Column chromatography (NH gel, 200–350 mesh, AcOEt/MeOH=10/1–5/1) afforded a product.

Free Base $^1$H-NMR (CD$_3$OD) δ 8.09 (d, J=8.6 Hz, 1H), 7.60 (d, J=8.6 Hz, 1H), 7.58 (dd, J=8.4, 1.0 Hz, 1H), 7.44 (t, J=8.2 Hz, 1H), 7.27 (dd, J=8.4, 1.0 Hz, 1H), 7.18 (d, J=1.0 Hz, 1H), 5.70–5.44 (m, 2H), 4.94 (dd, J=8.6, 3.6 Hz, 1 H), 3.65–3.30 (m, 6H), 2.94–2.60(m, 4H), 2.59 (s, 3H), 2.53 (s, 3H), 2.35–2.15 (m, 6H), 2.05–1.90 (m, 2H), 1.90–1.55 (m, 6H), 1.45–1.20 (m, 2H) HCl salt mp 181–184° C.

IR (KBr)v$_{max}$: 3386, 2924 1655, 1638, 1439, 1333, 1269, 1153, 1030 cm$^{-1.}$ MS (m/z): 686.18 (ES+, exact mass 685.23)

Example 2

N-[1-[[(2S)-1-[[2,4-DICHLORO-3-[[(2,4-DIMETHYL-8-QUINOLINYL)OXY]METHYL]PHENYL]SULFONYL]PYRROLIDINYL]CARBONYL]-3-AZETIDINYL]-EXO-8-METHYL-8-AZABICYCLO[3.2.1]OCTAN-3-AMINE

A. 1-Benzhydryl-3-azetidinol

A mixture of benzhydrylamine (25.0 g, 136 mmol), epichlorohydrine (12.6 g, 136 mmol) in MeOH (55 mL) was stirred for 3 days at room temperature. Then the mixture was stirred under reflux for 2 days. After cooling, the solvent was evaporated in vacuo and the resulting solid was washed with acetone (30 mL). Then the solid was suspended in Et$_2$O (500 mL) and washed with aqueous 6N NaOH (100 mL). The organic layer was dried over MgSO$_4$ and concentrated in vacuo to afford a product (13.6 g, 42%). This compound was used for the next reaction without further purification.

$^1$H-NMR (CDCl$_3$) 67 : 7.38–7.14 (m, 1OH), 4.46–4.37 (m, 1H), 4.34 (s, 1H), 3.53–3.47 (m, 2H), 3.13 (brs, 1H), 2.92–2.86 (m, 2H)

B. 1-Benzhydryl-3-azetidinone

To a stirred solution of oxalyl chloride (21.6 g, 170 mmol) in CH$_2$Cl$_2$ (270 mL) was added DMSO (26.6 g, 340 mmol) at −78° C. Then to the mixture was added dropwise a solution of 1-benzhydryl-3-azetidinol (13.6 g, 56.7 mmol) in CH$_2$Cl$_2$ (68 mL). After the mixture was stirred for 30 min, to the mixture was added triethylamine (51.6 g, 510 mmol) at −78° C., and the resulting mixture was warmed to room temperature and stirred for 30 min before H$_2$O (50 mL) was added. The organic layer was separated, washed with brine, dried over MgSO$_4$ and concentrated in vacuo. The residue was purified by column chromatography (SiO$_2$, 230–400 mesh, 300 g, Hexane/AcOEt=7/1 to 3/1) to give a product (10.0 g, 75%) as a yellow crystal.

$^1$H-NMR (CDCL$_3$) δ: 7.49–7.45 (m, 4H), 7.32–7.17 (m, 6H), 4.58 (s, 1 H), 3.99 (s, 4H)

C. N-(1-Benzhydryl-3-azetidinyl)-exo-8-methyl-8-azabicyclo[3.2.1]octan-3-amine To a stirred suspension of 1-benzhydryl-3-azetidinone (4.75 g, 20.0 mmol) and exo-3-aminotropane (2.80 g, 20.0 mmol) was added Ti(OiPr)$_4$ (8.9 mL, 30 mmol) and the mixture was stirred at room temperature for 4 h. Then to the mixture was added MeOH (90.0 mL) to dissolve the resulting precipitate. The mixture was treated carefully with NaBH$_4$ (1.14 g, 30.0 mmol) and stirred for 16 h at room temperature before adding saturated aqueous NaHCO$_3$ (10 mL). After the mixture was filtered through a pad of celite, the filtrate was concentrated in vacuo, The residue was purified by column chromatography (NH gel, 200–350 mesh, 120 g, CH$_2$Cl$_2$/MeOH=100/0 to 10/1) to give a product (3.45 g, 48%) as a white solid.

D. tert-Butyl 1-benzhydryl-3-azetidinyl[exo-8-methyl-8-azabicyclo[3.2.1]oct-3-yl]carbamate To a stirred solution of N-(1-benzhydryl-3-azetidinyl)-exo-8-methyl-8-azabicyclo[3.2.1]octan-3-amine (3.45 g, 9.54 mmol) in CH$_2$Cl$_2$ (19 mL) was added Boc$_2$O (2.08 g, 9.54 mmol) at room temperature and the mixture was stirred for 16 h before adding saturated aqueous NaHCO$_3$ (10 mL). The organic layer was extracted with CH$_2$Cl$_2$ (100 mL), dried over MgSO$_4$ and concentrated in vacuo. The residue was purified by column chromatography (NH gel, 200–350 mesh, 120 g, CH$_2$Cl$_2$/MeOH =100/0 to 50/1) to give a product (4.13 g, 94%) as a yellow oil.

$^1$H-NMR (CDCL$_3$) 67 : 7.41–7.38 (m, 4H), 7.28–7.13 (m, 6H), 4.46 (s, 1H), 4.23–4.08 (m, 2H), 3.39–3.30 (m, 4H), 3.17 (brs, 2H), 2.32 (s, 3H), 2.08–1.98 (m, 4H), 1.66–1.58 (m, 2H), 1.50 (s, 9H), 1.38–1.32 (m, 2H)

E. tert-Butyl 3-azetidinyl[exo-8-methyl-8-azabicyclo[3.2.1]oct-3-yl]carbamate A mixture of tert-butyl 1-benzhydryl-3-azetidinyl[exo-8-methyl-8-azabicyclo[3.2.1]oct-3-yl]carbamate (4.13 g, 8.95 mmol) and Pd(OH)$_2$-C (20 wt % on carbon, 2.0 g) in MeOH (41 mL) was stirred under hydrogen atmosphere (4 atm) at room temperature for 8 h. After the mixture was filtered through a pad of celite (30% MeOH-CH$_2$Cl$_2$, 20 mL), the filtrate was concentrated in vacuo. The residue was purified by column chromatography (NH gel, 200–350 mesh, 120 g, CH$_2$Cl$_2$/MeOH=100/0 to 10/1) to give a product (3.0 g, 100%) as a white solid.

F. N-[1-[[(2S)-1-[[2,4-Dichloro-3-[[(2,4-dimethyl-8-quinolinyl)oxy]methyl]phenyl]sulfonyl]pyrrolidinyl] carbonyl]-3-azetidinyl]-exo-8-methyl-8-azabicyclo[3.2.1]octan-3-amine The coupling product (N-Boc compound) was prepared by a procedure similar to that described in method A. Then the product was dissolved in 0.3 mL of MeOH, to which was added 4 N HCl/dioxane (150 μL, 600 μmol). The mixture was agitated by swirling for 16 h at room temperature and concentrated to dryness. The deBoc compound was purified according to the procedure described in method A.

MS (m/z): 686.59 (ES+, exact mass 685.23)

Example 3

(2S)-N-[2-(3,8-DIAZABICYCLO[3.2.1]OCT-3-YL)-2-OXOETHYL]-1-[[2,4-DICHLORO-3-[[(2,4-DIMETHYL-8-QUINOLINYL)OXY]METHYL]PHENYL]SULFONYL]-2-PYRROLIDINECARBOXAMIDE

A. Diethyl meso-1-Benzyl-2,5-pyrrolidinedicarboxylate

A solution of Diethyl meso-2,5-dibromoadipate (50 g, 139 mmol) in benzene (150 mL) was heated to reflux. Then heating was discontinued and benzylamine (50 mL) was added under stirring in 1 h. At the end of the addition, the mixture was refluxed for 20 h. After cooling down, the hydrobromide salt was filtered off and washed with benzene, and the benzene solution was evaporated. The residue was distilled under reduced pressure (180–190° C./0.3 mmHg) to give a product (39.9 g, 94%) as a yellow oil.

$^1$H NMR (CDCl$_3$, 270 MHz) δ: 7.35–7.24 (m, 5H), 4.15–3.97 (m, 4H), 3.93 (s, 2H), 2.10–2,05 (m, 4H), 1.24 (t, J =7.1 Hz, 3H), 1.19 (t, J =7.3 Hz, 3H)

B. Diethyl meso-2,5-Pyrrolidinedicarboxylate A mixture of diethyl meso-1-benzyl-2,5-pyrrolidinedicarboxylate (13.1 g, 43 mmol), Pd(OH)$_2$/C (20% wt, 6.5 g) in MeOH was hydrogenated at 4 atm for 5 h. The mixture was filtered through celite. The filtrate was concentrated in vacuo to give a product (26.3 g, 94%) as a light yellow oil.

$^1$H NMR (CDCl$_3$, 270 MHz) δ: 4.24–4.15 (m, 4H), 3.99–3.94 (m, 1H), 3.85–3.77 (m, 2H), 2.24–1.86 (m, 4H), 1.28 (t, J =7.1 Hz, 6H)

C . Ethyl (2S*, 5R*)-5-[(benzylamino)carbonyl]-2-Pyrrolidinedicarboxylate

A mixture of diethyl meso-2,5-pyrrolidinedicarboxylate (26.3 g, 122 mmol), benzyamine (13.1 g, 122 mmol) in xylene (80 mL) was refluxed for 18 h. After cooling down, a white solid was separated. The filtrate was evaporated and the residue was distilled under reduced pressure to remove the byproducts. (byproducts 1$^{st}$ fraction, 55° C./0.2 mmHg, 2$^{nd}$ fraction, 125° C./0.2 mmHg) The crude residue (33 g) was used for the next step.

D. 3-Benzyl-3,8-diazabicyclo[3.2.1]octane-2.4-dione

The crude ethyl (2S*, 5R*)-5-[(benzylamino)carbonyl]-2-Pyrrolidinedicarboxylate (33 g) was heated at 220° C. for 5 h. Then the residue was distilled under reduced pressure (175° C., 0.3 mHg) to give a yellow oil, which included a byproduct. Then a mixture of this yellow oil and the distillation residue was purified by column chromatography (SiO$_2$, 230–400 mesh, 30 g, Hexane/AcOEt=2/1 to AcOEt only) to give the desired pure product (2.74 g, 10%) as a yellow oil.

$^1$H NMR (CDCl$_3$, 270 MHz) δ: 7.31–7.23 (m, 5H), 4.80 (s, 2H), 4.15–4.11 (m, 2H), 2.26–2.15 (m, 2H), 1.95–1.88 (m, 2H)

E. 3-Benzyl-3,8-diazabicyclo[3.2.1]octane

To a stirred suspension of LiAlH$_4$ (1.37 g, 36.1 mmol) in dry Et$_2$O (23 mL) was added a solution of 3-benzyl-3,8-diazabicyclo[3.2.1]octane-2,4-dione (2.74 g, 11.9 mmol) in dry Et$_2$O (27.5 mL) dropwise at 0° C. Then the mixture was refluxed for 46 h. After cooling down, the mixture was quenched with H$_2$O (1.4 mL), 15% aq. NaOH (1.4 mL) and H$_2$O (4.1 mL) successively, filtered through celite. The filtrate was concentrated in vacuo to provide a product (2.3 g, 96%) as a yellow oil. This product was used for the next reaction without purification.

F. tert-Butyl 3-Benzyl-3,8-diazabicyclo[3.2.1]octane-8-carboxylate

To a stirred solution of 3-benzyl-3,8-diazabicyclo[3.2.1]octane (2.30 g, 11.4 mmol) in CH$_2$Cl$_2$ (23 mL) was added Boc$_2$O (2.48 g, 11.4 mmol), and the mixture was stirred at room temperature overnight. Then the mixture was treated with saturated aqueous NaHCO$_3$ and the organic layers were extracted with CH$_2$Cl$_2$, dried over MgSO$_4$, and concentrated in vacuo. The residue was purified with column chromatography (SiO$_2$, 230–400 mesh, 69 g, Hexane only to AcOEt/Hexane =1/201, then 1/10) to give a product (2.2 g, 65%) as a colorless oil.

$^1$H NMR (CDCl$_3$, 270 MHz) δ: 7.31–7.23 (m, 5H), 4.20–4.10 (m, 1H), 3.47 (s, 2H), 2.60 (dd, J=11.0, 3.0 Hz, 2H), 2.35–2.20 (m, 1 H), 1.92–1.77 (m, 4H), 1.46 (s, 9H)

G. tert-Butyl 3,8-diazabicyclo[3.2.1]octane-8-carboxylate

A mixture of tert-butyl 3-benzyl-3,8-diazabicyclo[3.2.1]octane-8-carboxylate, Pd(OH)$_2$-C (1.1 g) in MeOH (22 mL) was stirred under hydrogen atmosphere (4 atm) for 10 h at room temperature. The mixture was filtered through celite and the filtrate was concentrated in vacuo to give a product (1.45 g, 94%) as a white solid. This product was used for next step without purification.

H. tert-Butyl 3-[(1,3-dioxo-1,3-dihydro-2H-isoindol-2-yl)acetyl]-3,8-diazabicyclo[3.2.1]octane-8-carboxylate To a stirred solution of N-phthaloylglycine (725 mg, 3.53 mmol) and tert-butyl 3,8-diazabicyclo[3.2.1]octane-8-carboxylate (500 mg, 2.36 mmol) in CH$_2$Cl$_2$ (20 mL) were added HOBt (481 mg, 3.53 mmol) and WSC (677 mg, 3.53 mmol) at room temperature and the mixture was stirred overnight. To the mixture was added H$_2$O (5 mL) and the organic layer was separated, washed with saturated aqueous NaHCO$_3$, brine, dried over MgSO$_4$, filtered and concentrated in vacuo. Flash chromatography (SiO$_2$, 230–400 mesh, 309, CH$_2$Cl$_2$-MeOH=98/2 to 92/8) afforded the product as a white solid (713 mg, 81%).

$^1$H NMR (CDCl$_3$, 270 MHz) δ: 7.90–7.85 (m, 2H), 7.75–7.70 (m, 2H), 4.55 (d, J=14.7 Hz, 1H), 4.36 (d, J=14.7 Hz, 1H), 4.35–4.14 (m, 2H), 3.52 (s, 2H), 3.00–2.92 (m, 1H), 2.06–1.65 (m, 3H), 1.49 (s, 9H)

I. tert-Butyl 3-(aminoacetyl)-3.8-diazabicyclo[3.2.1]octane-8-carboxylate

To a stirred solution of tert-Butyl 3-[(1,3-dioxo-1,3-dihydro-2H-isoindol-2-yl)acetyl]-3,8-diazabicyclo[3.2.1]octane-8-carboxylate (70.0 mg, 0.187 mmol) in EtOH (1.9 mL) was added hydrazine monohydrate (19.0 mg, 0.375 mmol) at room temperature and the mixture was refluxed for 1 h. After cooling, the precipitates formed were filtered off. The filtrate was evaporated in vacuo and the residue was purified by preparative TLC (SiO$_2$, 20×20 cm, 1 mm, CH$_2$Cl$_2$/MeOH/aqueous NH$_3$=92/6/2) to afford a product (21.4 mg, 42%) as a white solid.

$^1$H NMR (CDCl$_3$, 270 MHz) δ: 4.30–4.20 (m, 3H), 3.50 (d, J=17.0 Hz, 1H), 3.35 (d, J=17.0 Hz, 1H), 3.36–3.30 (m,

2H), 3.00–2.87 (m, 2H), 2.00–1.90 (m, 2H), 1.72–1.58 (m, 2H), 1.48 (s, 9H)

J. (2S)-N-[2-(3,8-Diazabicyclo[3.2.1]oct-3-yl)-2-oxoethyl]-1-[[2,4-dichloro-3-[[(2,4-dimethyl-8-quinolinyl)oxy]methyl]phenyl]sulfonyl]-2-pyrrolidinecarboxamide The titled compound was prepared by a procedure similar to that described in method A.

MS (m/z): 660.37 (ES+, exact mass 659.17)

Example 4

(2S)-1-[[2,4-DICHLORO-3-[[(2,4-DIMETHYL-8-QUINOLINYL)OXY]METHYL]PHENYL]SULFONYL]-N-[EXO-2-[(8-METHYL-8-AZABICYCLO[3.2.1]OCT-3-YL)AMINO]-2-OXOETHYL]-2-PYRROLIDINECARBOXAMIDE, HCl SALT

A. Benzylexo-3-[(8-methyl-8-azabicyclo[3.2.1]oct-3-yl)amino]-2-oxoethylcarbamate To a solution of N-Cbz-glycine (3.58 g, 17.1 mmol) and exo-3-aminotropane[2] (2.00 g, 14.3 mmol) in $CH_2Cl_2$ (71 mL) was added WSC (3.01 g, 15.7 mmol) at room temperature. After stirred at room temperature for 18 h, the reaction mixture was diluted with water (50 mL) and stirred at room temperature for 30 minute. The water phase was separated and extracted with $CH_2Cl_2$ (50 mL×2). The combined organic phase was washed with brine, dried over $MgSO_4$ and concentrated in vacuo. Flash chromatography of the residue (NH gel, 200–350 mesh, 150 g, $CH_2Cl_2$/MeOH =100/1 to 50/1) afforded a product (2.18 g , 46%) as a colorless oil.

$^1$H NMR (CDCl$_3$, 270 MHz) δ: 7.41–7.29 (m, 5 H), 5.76 (brs, 1 H), 5.46 (brs, 1 H), 5.12 (s, 2 H), 4.20–4.01 (m, 1 H), 3.80 (d, J =5.5 Hz, 2 H), 3.19–3.09 (m, 2 H), 2.26 (s, 3 H), 2.09–1.96 (m, 2 H), 1.86–1.40 (m, 6 H)

B. Exo-2-amino-N-(8-methyl-8-azabicyclo[3.2.1.]oct-3-yl)ethanamide

A mixture of benzyl exo-3-[(8-methyl-8-azabicyclo[3.2.1]oct-3-yl)amino]-3-oxopropylcarbamate (2.71 g, 8.17 mmol) and 10% Pd on carbon (8.13 mg) in MeOH (17 mL) was stirred under hydrogen atmosphere (1 atm) at room temperature for 18 h. Catalyst was removed by filtration and the filtrate was concentrated in vacuo to afford a product 1.48 g as a colorless oil. This crude product was used for the next reaction without further purification.

$^1$H NMR (CDCl$_3$, 270 MHz) 5: 4.30–4.10 (m, 1 H), 3.27 (s, 2 H), 3.30–3.10 (m, 2 H), 2.41 (s, 3 H), 2.18–2.10 (m, 2 H), 1.90–1.60 (m, 6 H)

C (2S)-1-[[2,4-Dichloro-3-[[(2,4-dimethyl-8-quinolinyl)oxy]methyl]phenyl]sulfonyl]-N-[exo-2-[(8-methyl-8-azabicyclo[3.2.1]oct-3-yl)amino]-2-oxoethyl]-2-pyrrolidinecarboxamide, HCl salt The title compound was prepared by a procedure similar to that described in method A-I Free Base $^1$H-NMR (CDCl$_3$) 67 : 8.12 (d, J=8.7 Hz, 1H), 7.62 (d, J=8.4 Hz, IH), 7.57 (d, J=8.4 Hz, 1H), 7.43 (t, J=7.9 Hz, 1H), 7.25–7.17 (m, 2H), 7.16 (s, 1H), 7.01 (t, J =5.5 Hz, 1H), 5.65–5.54 (m ,2H), 4.43 (dd, J=6.8, 4.6 Hz, 1H), 4.10–3.92 (m, 2H), 3.83 (dd, J=5.2, 16.8 Hz, 1H), 3.67–3.57 (m, 1H), 3.49 (dd, J=7.8, 16.1 Hz, 1H), 3.05 (brs, 2H), 2.65 (brs, 6H), 2.17 (s, 3H), 2.20–2.15 (m, 2H), 2.02–1.90 (m, 4H), 1.75–1.57 (m, 4H), 1.25 (t, J=7.5 Hz, 2H)

MS (m/z): 688.18 (ES+, exact mass 687.20)

HCl salt mp 190–192° C.

Example 5

(2S)-1-[[-1-[[2,4-DICHLORO-3-[[(2,4-DIMETHYL-8-QUINOLINYL)OXY]METHYL]PHENYL]SULFONYL]PYRROLIDINYL]CARBONYL]-4-PIPERIDINOPIPERIDINE, HCl SALT

The title compound was prepared by a procedure similar to that described in method A.

Free Base

MS (m/z): 659.19 (ES+, exact mass 658.21)

$^1$H-NMR (CDCl$_3$) δ: 8.16 (d, J=8.6 Hz, 1H), 7.61 (d, J=8.4 Hz, 1H), 7.46 (d, J=8.4 Hz, 1H), 7.40 (t, J=8.2 Hz, 1H), 7.24 (d, J=8.6, 1.0 Hz, 1H), 7.14 (s, 1H), 5.70–5.44 (m ,2H), 5.66 (s, 2H), 5.04–4.95 (m, 1 H), 4.60–4.50 (m, 1 H), 4.00–3.77 (m, 1 H), 3.54–3.25 (m, 1 H), 3.51–3.43 (m, IH), 3.15–2.90 (m, 2H), 2.68 (s, 3H), 2.65(s, 3H), 2.60–2.40 (m, 5H), 2.30–1.30 (m, 14H)

HCl salt mp 163–167° C.

Example 6

(2S)-1-[[3-[(2,4-DIMETHYLQUINOLIN-8-YL)OXYMETHYL]-2,4-DICHLOROPHENYL]SULFONYL]-[3-[[(3-AMINOCYCLOHEXYL)CARBONYL]AMINO]PROPYL]-2-PYRROLIDINECARBOXAMIDE, HCl SALT

A. 3-[(tert-Butoxycarbonyl)amino]cyclohexanecarboxylic acid

To a suspension of 3-aminocyclohexanecarboxylic acid (0.72 g, 5.0 mmol) in dioxane-$H_2O$ (10 mL-5 mL) were added 1N aqueous NaOH (5.0 mL, 5.0 mmol) and di-tert-butyl dicarbonate (1.2 g , 5.3 mmol) at 0° C. The mixture was stirred for 1 day at room temperature, and concentrated in vacuo. The residue was diluted with $H_2O$, acidified with 10% aqueous citric acid, and extracted with AcOEt. The extract was dried over $MgSO_4$, and filtered. Removal of solvent gave a product (0.97 g, 76%) as a white solid.

$^1$H-NMR (CDCl$_3$) 67 : 4.55–4.40 (1H, m), 3.55–3.35 (1H, m), 2.50–2.20 (2H, m), 2.03–1.80 (3H, m), 1.44 (9H, s), 1.40–0.95 (4H, m).

B. (2S)-1-[[(3-[(2,4-Dimethylquinolin-8-yl)oxymethyl]-2,4-dichlorophenyl]sulfonyl]-N-[3-[[3-[(tert-butoxycarbonyl)amino]cyclohexylcarbonyl]amino]propyl]-2-pyrrolidinecarboxamide To a stirred mixture of (2S)-1-[[3-[(2,4-dimethylquinolin-8-yl)oxymethyl]-2,4-dichlorophenyl]sulfonyl]-N-(3-aminopropyl)-2-pyrrolidinecarboxamide dihydrochloride[1] in $CH_2Cl_2$ (3 mL) was added triethylamine (33 μl, 0.23 mmol) at room temperature. After stirring for 10 min, 3-[(tert-butoxycarbonyl)amino]cyclohexanecarboxylic acid (example6-A, 23 mg, 0.094 mmol), 1-hydroxybenzotriazole (13 mg, 0.094 mmol) and WSC (18 mg, 0.094 mmol) were added at room temperature. The mixture was stirred for 18 h, washed with $H_2O$ and saturated aqueous $NaHCO_3$. After removal of solvent, the residual oil was purified by column chromatography (SiO2, 230–400 mesh, 1.5 g, $CH_2Cl_2$/MeOH =99/1 to 90/10) to provide a product (50 mg, 81%) as a colorless oil.

$^1$H-NMR (CDCl$_3$) 67 : 8.11 (1H, d, J=8.6 Hz), 7.64 (IH, d, J=8.2 Hz), 7.55 (1H, d, J=8.6 Hz), 7.44 (1H, t, J=8.2 Hz), 7.25 (1H, d, J=8.2 Hz), 7.16 (IH, s), 6.95–6.85 (1H, m), 6.65–6.50 (1H, m), 5.66 (2H, s), 4.54–4.40 (2H, m), 3.65–3.05 (7H, m), 2.66 (3H, s), 2.65 (3H, s), 2.30–0.90 (15H, m), 1.43 (9H, s)

C. (2S)-1-[[3-[(2,4-Dimethylquinolin-8-yl)oxymethyl]-2,4-dichlorophenyl]sulfonyl]-N-[3-[[(3-aminocyclohexyl)carbonyl]amino]propyl]-2-pyrrolidinecarboxamide, HCl salt To a stirred solution of (2S)-1-[[3-[(2,4-dimethylquinolin-8-yl)oxymethyl]-2,4-dichlorophenyl]sulfonyl]-N-[3-[[3-[(tert-butoxycarbonyl)amino]cyclohexylcarbonyl]amino]propyl]-2-pyrrolidinecarboxamide (50 mg, 0.063 mmol) in MeOH (3 mL) was added HCl-MeOH (1 mL) at room temperature, and the mixture was stirred for 18 h. After removal of solvent, the residual solid was triturated with AcOEt, and collected to give a product (38 mg, 79%) as a white solid.

Free Base $^1$H-NMR (CDCl$_3$) δ: 8.11 (1H, d, J=8.6 Hz), 7.64 (IH, d, J=8.2 Hz), 7.56 (1H, d, J=8.6 Hz), 7.44 (IH, t, J=8.2 Hz), 7.25 (1H, d, J=8.2 Hz), 7.17 (1H, s), 7.00–6.90 (1H, m), 6.70–6.55 (1H, m), 5.64 (2H, s), 4.51 (1H, dd, J=3.2,8.2 Hz), 3.65–3.05 (7H, m), 2.66 (3H, s), 2.65 (3H, s), 2.30–0.90 (15H, m)

MS (m/z): 690.22 (ES+, exact mass 689.22)

The chemical structures of the compounds prepared in the Examples 1 to 6 are summarized in the following table.

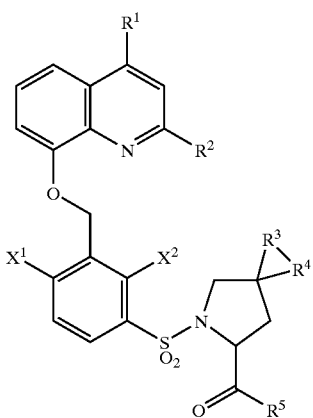

(wherein X$^1$ and X$^2$ are chloro; R$^1$ and R$^2$ are methyl; and R$^3$ and R$_4$ are hydrogen)

TABLE

| Ex. # | R$^5$ |
|---|---|
| 1 | 4-(1-azabicyclo[2.2.2]octy-3-yl)-piperazin-1-yl |
| 2 | 8-azabicylo[3.2.1]octanylaminoazetidin-1-yl |
| 3 | 2-(3,8-diazabicyclo[3.2.1]oct-3-yl)-2-oxomethylamino |
| 4 | 8-methyl-8-azabicyclo[3.2.1]oct-3-yl-aminooxomethylamino |
| 5 | piperidinopiperidinyl |
| 6 | [[(3-aminocyclohexyl)carbonyl]amino]propylamino |

What is claimed is:
1. A compound of the formula (I):

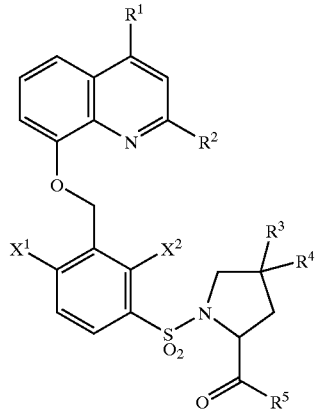

or a pharmaceutically acceptable salt thereof wherein
X$^1$ and X$^2$ are independently halo or C$_{1-4}$ alkyl;
R$^1$ and R$^2$ are independently hydrogen or C$_{1-4}$ alkyl;
R$^3$ and R$^4$ are independently hydrogen or halo; and
R$^5$ is
(a) —C$_{3-9}$ diazacycloalkyl optionally substituted with C$_{5-11}$ azabicycloalkyl;
(b) —C$_{3-9}$ azacycloalkyl-NH—(C$_{5-11}$ azabicycloalkyln optionally substituted with C$_{1-4}$ alkyl);
(c) —NH—C$_{1-3}$ alkyl-C(O)—C$_{5-11}$ diazabicycloalkyl;
(d) —NH—C$_{1-3}$ alkyl-C(O)—C$_{4-9}$ azabicycloalkyl, the —C$_{5-11}$ azabicycloalkyl being optionally substituted with C$_{1-4}$ alkyl;
(e) —C$_{3-9}$ azacycloalkyl optionally substituted with C$_{3-9}$ azacycloalkyl; or
(f) —NH—C$_{1-5}$ alkyl-NH—C(O)—C$_{4-9}$ cycloalkyl-NH$_2$.
2. A compound according to claim 1, wherein
X$^1$ and X$^2$ are chloro;
R$^1$ and R$^2$ are independently hydrogen, methyl or ethyl;
R$^3$ and R$^4$ are independently hydrogen or fluoro; and
R$^5$ is —C$_{4-8}$ diazacycloalkyl substituted with C$_{3-10}$ azabicycloalkyl.
R$^5$ is
(a) —C$_{4-8}$ diazacycloalkyl optionally substituted with C$_{6-10}$ azabicycloalkyl;
(b) —C$_{3-6}$ azacycloalkyl-NH—(C$_{6-10}$ azabicycloalkyln optionally substituted with C$_{1-4}$ alkyl);
(c) —NH—C$_{1-3}$ alkyl-C(O)—C$_{6-10}$ diazabicycloalkyl;
(d) —NH—C$_{1-3}$ alkyl-C(O)—C$_{6-10}$ azabicycloalkyl, the —C$_{6-10}$ azabicycloalkyl being optionally substituted with C$_{1-4}$ alkyl;
(e) —C$_{4-8}$ azacycloalkyl optionally substituted with C$_{4-8}$ azacycloalkyl; or
(f) —NH—C$_{1-5}$ alkyl-NH—C(O)—C$_{5-8}$ cycloalkyl-NH$_2$.
3. A compound according to claim 2, wherein
R$^1$ and R$^2$ are methyl; R$^3$ and R$^4$ are hydrogen; and
R$^5$ is azabicyclo[2.2.2]octyl-piperazinyl, azabiclyo[3.2.1]octanylaminoazetidinyl, diazabicyclo[3.2.1]octyl-oxomethylamino, diazabicyclo[3.2.1]octyl-oxoethylamino, methylazabicyclo[3.2.1]octyl-aminooxomethylamino, methylazabicyclo[3.2.1]octyl-aminooxomethylamino, ethylazabicyclo[3.2.1]

octyl-aminooxomethylamino, piperidinopiperidinyl, [[(aminocyclohexyl)carbon]amino]propylamino [[(aminocyclo hexyl)carbon]amino]butylamino.

4. A compound according to claim 3, wherein $R^5$ is azabicyclo[2.2.2]oct-3-yl]-1-piperazinyl, azabicyclo[3.2.1]octanylaminoazetidinyl, diazabicyclo[3.2.1]octyl- oxomethylamino, methylazabicyclo[3.2.1]octyl-aminooxomethylamino, piperidinopiperidinyl or [[(aminocyclohexyl)carbonyl]amino]propylamino.

5. A compound according to claim 1 selected from 8-[[3-[[(2S)-2-[[4-[(3S)-1-azabicyclo[2.2.2]oct-3-yl]-1-piperazinyl]carbonyl]pyrrolidinyl]sulfonyl]-2,6-dichlorobenzyl]oxy]-2,4-dimethylquinoline; (2S)-N-[2-(3,8-Diazabicyclo[3.2.1]oct-3-yl)-2-oxoethyl]-1-[[2,4-dichloro-3-[[(2,4-dimethyl-8quinolunyl)oxy]methyl]phenyl]sulfonyl]-2pyrrolidinexcarboxamide, and or a salt thereof.

* * * * *